(12) United States Patent
Jiang et al.

(10) Patent No.: US 11,432,749 B2
(45) Date of Patent: Sep. 6, 2022

(54) NON-CONTACT BRAIN BLOOD OXYGEN DETECTING SYSTEM

(71) Applicant: INSTITUTE OF AUTOMATION, CHINESE ACADEMY OF SCIENCES, Beijing (CN)

(72) Inventors: Tianzi Jiang, Beijing (CN); Xin Zhang, Beijing (CN); Nianming Zuo, Beijing (CN)

(73) Assignee: INSTITUTE OF AUTOMATION, CHINESE ACADEMY OF SCIENCES, Beijing (CN)

(*) Notice: Subject to any disclaimer, the term of this patent is extended or adjusted under 35 U.S.C. 154(b) by 173 days.

(21) Appl. No.: 16/958,706

(22) PCT Filed: Dec. 28, 2017

(86) PCT No.: PCT/CN2017/119296
§ 371 (c)(1),
(2) Date: Jun. 28, 2020

(87) PCT Pub. No.: WO2019/127194
PCT Pub. Date: Jul. 4, 2019

(65) Prior Publication Data
US 2020/0352491 A1  Nov. 12, 2020

(51) Int. Cl.
*A61B 5/1455* (2006.01)
*A61B 5/00* (2006.01)

(52) U.S. Cl.
CPC .......... *A61B 5/14553* (2013.01); *A61B 5/002* (2013.01); *A61B 5/14552* (2013.01);
(Continued)

(58) Field of Classification Search
CPC .............. A61B 5/1455; A61B 5/14552; A61B 5/14553; A61B 5/742; A61B 5/7475; A61B 5/6898
See application file for complete search history.

(56) References Cited

U.S. PATENT DOCUMENTS 7,840,257 B2 * 11/2010 Chance ................ A61B 5/6834
600/476
9,039,179 B2 * 5/2015 Brown, Jr. ........... A61B 3/0025
351/208
(Continued)

FOREIGN PATENT DOCUMENTS

CN           1326328 A      12/2001
CN        204394527 U        6/2015
(Continued)

*Primary Examiner* — Eric F Winakur
(74) *Attorney, Agent, or Firm* — Bayramoglu Law Offices LLC

(57) ABSTRACT

A non-contact brain blood oxygen detecting system includes a mobile terminal device. The mobile terminal device includes a control module, a transmitting module, a receiving module and a display module. The control module is connected to the transmitting module, the receiving module and the display module, respectively. The transmitting module in the mobile terminal device is configured to emit dual-wavelength near-infrared light to a detected subject. The receiving module is configured to receive a light signal after propagation fed back by the detected subject, and to perform data conversion on the received light signal to obtain a digital signal containing blood oxygen information. The control module is configured to obtain the blood oxygen information of the detected subject according to the digital signal obtained by the receiving module. The display module is configured to display the blood oxygen information obtained by the control module.

14 Claims, 2 Drawing Sheets

(52) U.S. Cl.
CPC ............ *A61B 5/742* (2013.01); *A61B 5/7475* (2013.01); *A61B 2560/0214* (2013.01); *A61B 2560/0443* (2013.01); *A61B 2560/0475* (2013.01); *A61B 2562/0238* (2013.01); *A61B 2562/0242* (2013.01); *A61B 2562/185* (2013.01); *A61B 2562/227* (2013.01)

(56) References Cited

U.S. PATENT DOCUMENTS

| | | | |
|---|---|---|---|
| 10,413,226 B2 * | 9/2019 | Tao | A61B 5/14552 |
| 2008/0017800 A1 | 1/2008 | Benni | |
| 2013/0204105 A1 | 8/2013 | Benni | |
| 2014/0275832 A1 * | 9/2014 | Muehlsteff | A61B 5/6889 |
| | | | 600/301 |
| 2015/0308946 A1 | 10/2015 | Duffy et al. | |

FOREIGN PATENT DOCUMENTS

| | | |
|---|---|---|
| CN | 105997102 A | 10/2016 |
| CN | 106236060 A | 12/2016 |

\* cited by examiner

NON-CONTACT BRAIN BLOOD OXYGEN DETECTING SYSTEM

CROSS REFERENCE TO THE RELATED APPLICATIONS

This application is the national phase entry of International Application No. PCT/CN2017/119296, filed on Dec. 28, 2017, the entire contents of which are incorporated herein by reference.

TECHNICAL FIELD

The present invention relates to the medical device field of blood oxygen detection, and more particularly, to a non-contact brain blood oxygen detecting system.

BACKGROUND

The human brain consumes twenty percent of the total oxygen required for healthy bodily function. Adequately monitoring and detecting blood oxygen levels in the brain are sometimes especially necessary and important. During surgery on the brain or heart, for example, patients may experience problems in surgery or afterward in recovery if brain nervous tissue is damaged by lack of oxygen. This can be especially problematic for patients undergoing surgery necessitated by cardiovascular and cerebrovascular diseases and traumatic brain injury. It is, therefore, highly desirable to provide optimal detection and monitoring of brain blood oxygen. At present, the non-invasive methods for detecting brain blood oxygen content are based upon the absorption characteristics of hemoglobin in brain nervous tissue. Wavelengths of light in the red and near-infrared spectrum are used to detect blood oxygen content. However, the current brain blood oxygen detecting products need to be in physical contact with the patient, such as fixing the optrode and the detector on the scalp for example. When procedures or other circumstances require blood oxygen detection for long time periods, the attached devices can become uncomfortable or even result in pain or injury to the patient, or subject.

SUMMARY

In order to solve the above problems in the prior art, i.e. to solve the technical problem of how to detect the blood oxygen content of brain blood oxygen in human body conveniently and safely, the present invention provides a non-contact brain blood oxygen detecting system.

A non-contact brain blood oxygen detecting system of the present invention includes a mobile terminal device, wherein the mobile terminal device includes a control module, a transmitting module, a receiving module and a display module; the control module is connected to the transmitting module, the receiving module and the display module, respectively;

the transmitting module is configured to emit dual-wavelength near-infrared light to a detected subject;

the receiving module is configured to receive a light signal after propagation fed back by the detected subject, and to perform data conversion on the received light signal to obtain a digital signal containing blood oxygen information;

the control module is configured to obtain the blood oxygen information of the detected subject according to the digital signal obtained by the receiving module; and the display module is configured to display the blood oxygen information obtained by the control module.

Further, a preferred technical solution provided by the present invention is as follows:

a rotation mechanism is arranged on a transmitter of the transmitting module and a receiver of the receiving module, respectively, and the rotation mechanism is controlled to rotate a specific angle to change a transmitting direction of the transmitter and a receiving direction of the receiver.

Further, a preferred technical solution provided by the present invention is as follows:

a light filter is arranged on the receiver of the receiving module to filter out an interference light signal.

Further, a preferred technical solution provided by the present invention is as follows:

the mobile terminal device further includes a memory module, a clock module, a power supply module and a communication module; wherein, the memory module is configured to store working data of the mobile terminal device;

the clock module is configured to provide a working clock signal to the mobile terminal device;

the power supply module is configured to supply power to the mobile terminal device; and the communication module is configured to communicate with an external device.

Further, a preferred technical solution provided by the present invention is as follows:

the power supply module includes a battery and a charging interface, and the charging interface is configured to connect to an external power source to charge the battery; and the charging interface is a USB interface, and the charging interface is further configured to communicate with the external device.

Further, a preferred technical solution provided by the present invention is as follows:

the communication module is a Bluetooth communication module.

Further, a preferred technical solution provided by the present invention is as follows:

the mobile terminal device further includes a control panel, and a plurality of preset control buttons are arranged on the control panel; and the preset control buttons are configured to control the mobile terminal device to perform corresponding operations.

Further, a preferred technical scheme provided by the present invention is as follows:

the number of the transmitting module is 1, and the number of the receiving modules is 2.

Further, a preferred technical scheme provided by the present invention is as follows:

a passband range of the light filter is 600-1000 nm.

Further, a preferred technical scheme provided by the present invention is as follows:

the system further includes a processing device, and the processing device is connected to and communicates with the mobile terminal device; and the processing device is configured to receive blood oxygen information obtained by the control module in the mobile terminal device, and to perform data analysis on and display the blood oxygen information received.

Compared with the closest available technology, the above technical solutions have at least the following advantages.

1. When the mobile terminal device in the present invention is used to perform blood oxygen detection on the detected subject, the transmitter of the transmitting module and the receiver of the receiver module are not required to be placed on or in contact with the subject, so as to not cause discomfort, injury or harm to the detected subject.

2. Both the transmitting module and the receiving module of the mobile terminal device of the present invention include a rotation mechanism, through which the transmitting direction and receiving direction of the signal can be freely adjusted to detect the blood oxygen information of different detected subjects and/or the blood oxygen information of different regions in the same detected subject.

3. The receiving module of the mobile terminal device in the present invention includes a light filter for filtering the interference light signal in the current environment, which overcomes the problem of test light saturation caused by excessive interference light signal.

4. In the present invention, the non-contact brain blood oxygen detecting system uses continuous wave (CW) technology. Specifically, the mobile terminal device includes one transmitting module and two receiving modules, which can transmit and receive simultaneously two different wavelengths of near-infrared light without setting a signal modulation and demodulation circuit thus simplifying the structure of the system and reducing costs.

5. In the present invention, the mobile terminal device can (i) display the blood oxygen information through the display module and (ii) send the blood oxygen information to the processing device for in-depth data analysis thus realizing a dual-purpose function of the detecting system.

DETAILED DESCRIPTION OF THE PRESENT EMBODIMENTS

Preferred embodiments of the present invention will be described hereinafter with reference to the drawings. It should be understood by those skilled in the art that these embodiments are only used to explain the technical principles of the present invention and are not intended to limit the scope of protection of the present invention.

Current brain blood oxygen detecting systems based on continuous wave (CW) of condensation technique detect brain blood oxygen information by attachment of an optrode and a detector onto the head so they are in contact with the skin and head of the detected subject. This kind of direct-contact detection not only increases the discomfort of the subject, but also may cause injury or harm to the subject. In this regard, the present invention provides a non-contact brain blood oxygen detecting system, which can accurately detect the brain blood oxygen information without attaching the optrode and the detector onto the head and skin.

One embodiment of the non-contact brain blood oxygen detecting system is described below in combination with the FIGS. 1-3.

Figure 1:
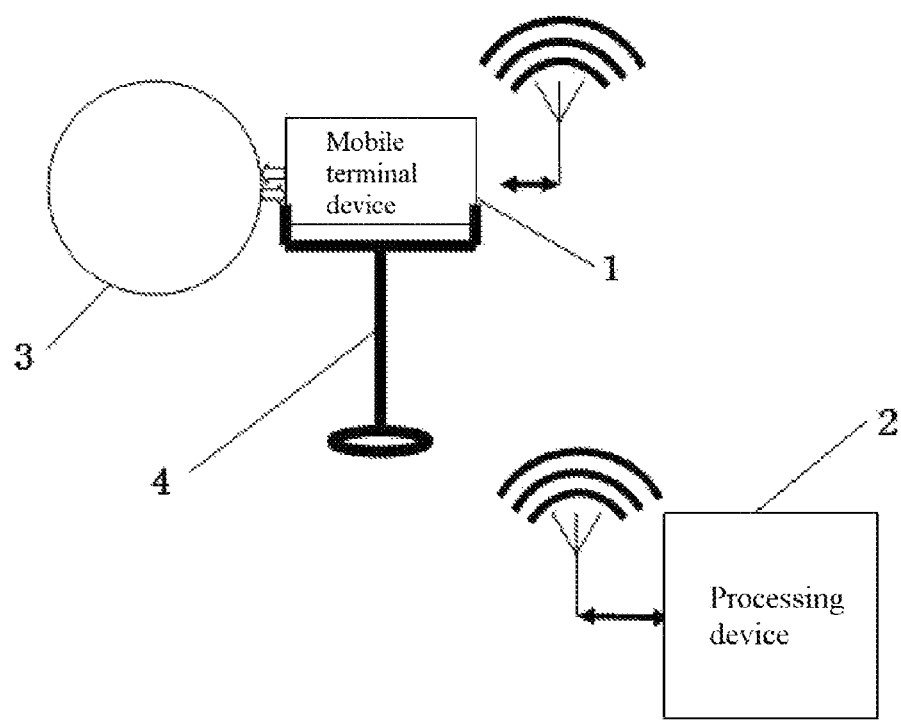
FIG. 1 is a schematic diagram showing a main structure of a non-contact brain blood oxygen detecting system according to an embodiment of the present invention.

Referring to FIG. 1, FIG. 1 is a schematic diagram showing a main structure of a non-contact brain blood oxygen detecting system in the present embodiment. As shown in FIG. 1, in the present embodiment, the non-contact brain blood oxygen detecting system includes the mobile terminal device 1 and the processing device 2. The mobile terminal device 1 is configured to detect the blood oxygen information of the detected subject 3 and send the detected blood oxygen information to the processing device 2 through wireless communication. Meanwhile, in the present embodiment, the mobile terminal device 1 can also be fixed on the bracket 4, thereby eliminating the detecting error caused by unsteadiness of the operator's hand(s) when holding the mobile terminal device 1. In the present embodiment, the detected subject 3 may be a human brain. The processing device 2 is configured to receive the blood oxygen information obtained by the mobile terminal device 1, perform data analysis on and display the blood oxygen information received.

Figure 2:
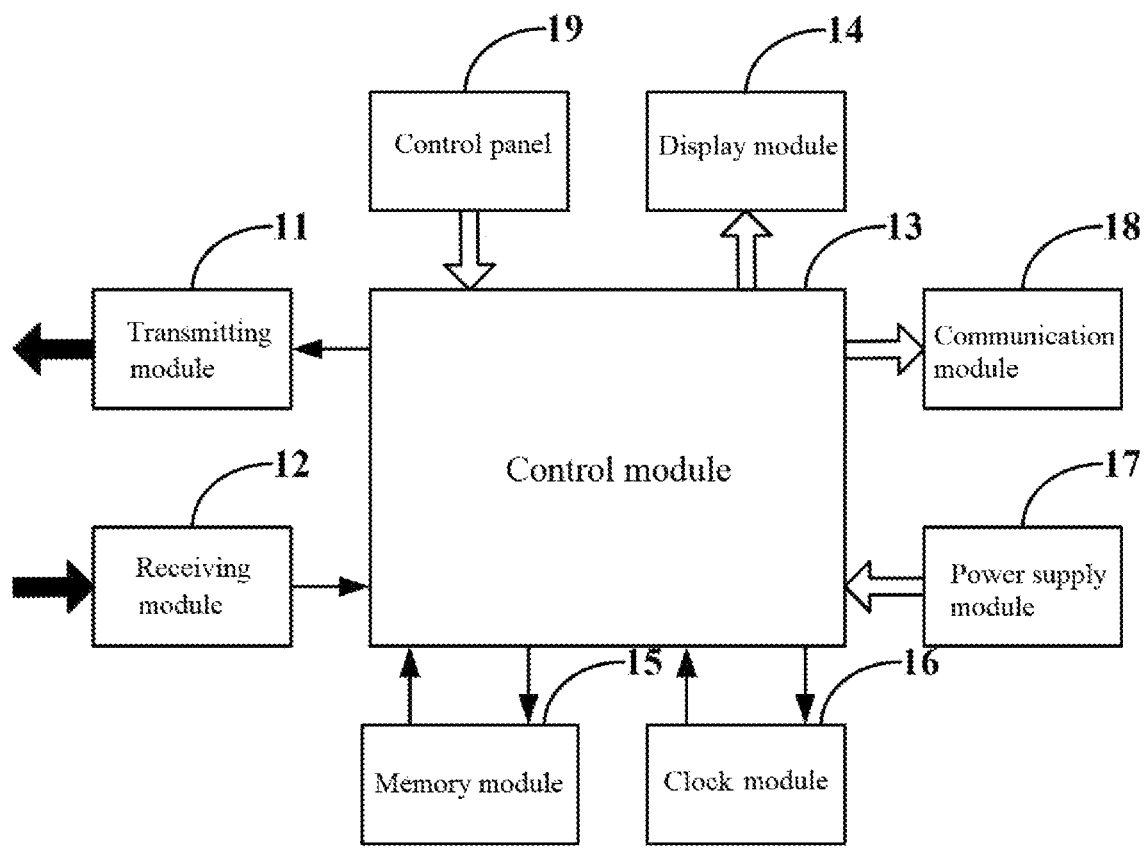
FIG. 2 is a schematic diagram showing a main structure of a mobile terminal device according to an embodiment of the present invention.

Referring to FIG. 2, FIG. 2 is a schematic diagram showing a main structure of the mobile terminal device in the present embodiment. As shown in FIG. 2, the mobile terminal device 1 of FIG. 1 of the present embodiment includes the transmitting module 11, the receiving module 12, the control module 13, the display module 14, the memory module 15, the clock module 16, the power supply module 17, the communication module 18, and the control panel 19.

In the present embodiment, the transmitting module 11 is configured to emit dual-wavelength near-infrared light to the detected subject 3, wherein the dual-wavelength near-infrared light has constant frequency and power. In the present embodiment, continuous wave technology can be adopted to emit the aforementioned dual-wavelength near-infrared light.

In the present embodiment, the receiving module 12 is configured to receive a light signal feedback after propagation from the detected subject 3, and to perform data conversion on the received light signal to obtain a digital signal containing blood oxygen information. Specifically, the receiving module 12 can receive the light signal which is fed back after the dual-wavelength near-infrared light is scattered and absorbed by a human brain. Moreover, in the present embodiment, the receiving module 12 can convert the received light signal through a positive-intrinsic-negative (PIN) diode to an electrical signal, and then convert the electrical signal through an analog-to-digital conversion unit to obtain a digital signal containing blood oxygen information.

Figure 3:
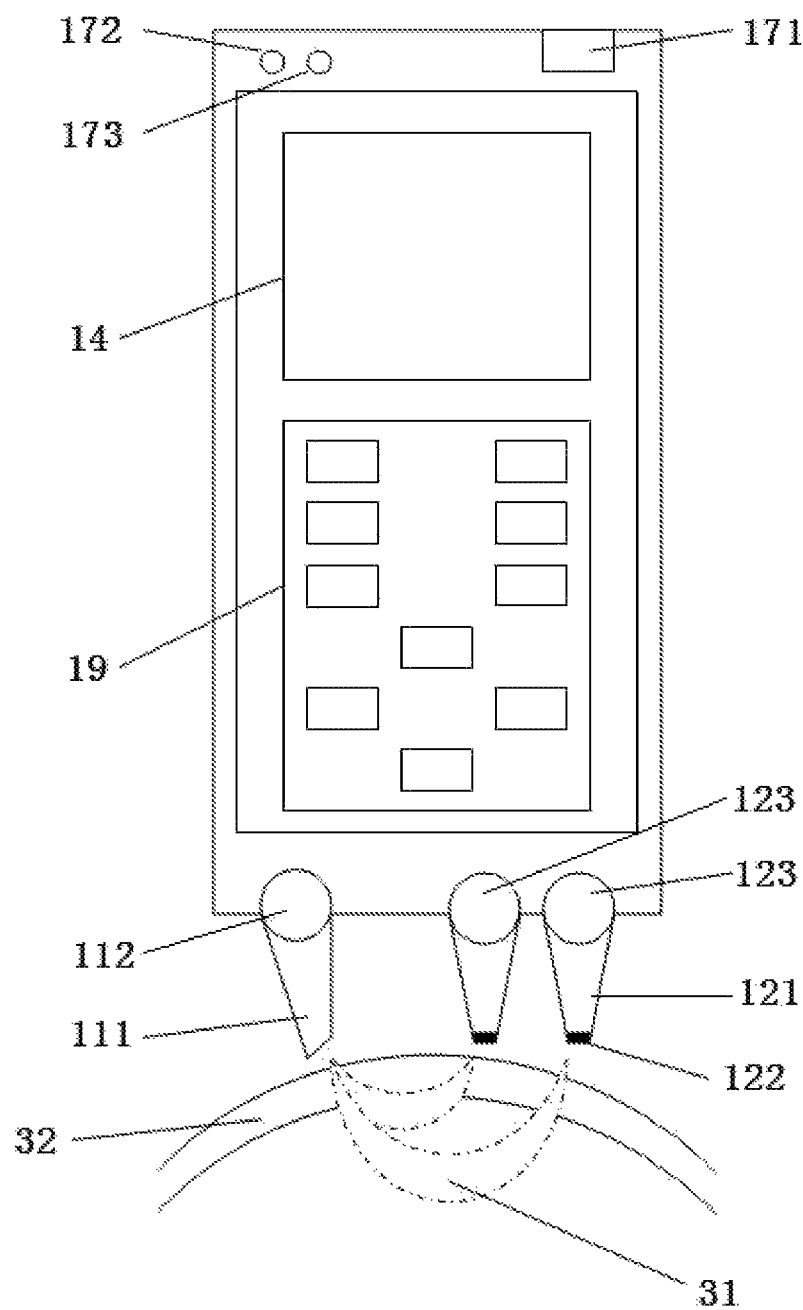
FIG. 3 is a schematic diagram showing a main structure of another mobile terminal device according to an embodiment of the present invention.

With reference to FIG. 3, FIG. 3 is a schematic diagram showing a main structure of another mobile terminal device in the present embodiment. As shown in FIG. 3, in the present embodiment, the mobile terminal device includes one transmitting module and two receiving modules, wherein the rotation mechanism 112 is arranged on the transmitter 111 of the transmitting module 11, and the light filter 122 and the rotation mechanism 123 are arranged on the receiver 121 of the receiving module 12. In the present embodiment, the rotation mechanism 112 is controlled to rotate a specific angle to change the transmitting direction of the transmitter 111. The rotation mechanism 123 is controlled to rotate a specific angle to change the receiving direction of the receiver 121. As shown in FIG. 3, the rotation mechanism 112 is controlled to rotate to adjust the direction of the transmitter 111 toward the brain cranium 31 of the detected subject, the rotation mechanism 123 is controlled to rotate to adjust the direction of the receiver 121 toward the brain cranium 31, thus detecting the blood oxygen information of different detection sites 31 of the detected subject. Moreover, in the present embodiment, the light filter 122 is arranged on the receiver 121 to filter out the interference light signal in the current environment, such as those of indoor lamps. In a preferred solution of the present embodiment, a light filter with a pass band range of 600 to 1000 nm can be adopted, while the distances between the two receivers 121 and the transmitter 111 are 3 cm and 4 cm, respectively.

In the present embodiment, the control module 13 is configured to obtain the blood oxygen information of the detected subject 3 shown in FIG. 1 according to the digital signal obtained by the receiving module 12. For example, the control module 13 can calculate the oxyhemoglobin saturation of the detected subject 3. Moreover, in the present embodiment, the control module 13 can send the blood oxygen information obtained to the display module 13 for display, and transfer the information to the memory module 15 for storage, and to the processing device 2 shown in FIG. 1 for data analysis. Further, in the present embodiment, the memory module 15 is configured to store all the work data of the mobile terminal device 1.

In the present embodiment, the clock module 16 is configured to provide a working clock signal to enable the mobile terminal device 1 to work normally. The power supply module 17 is configured to supply power to the mobile terminal device 1. The communication module 18 is configured to communicate with an external device, such as the processing device 2 shown in FIG. 1. In a preferred solution of the present embodiment, the communication module is a Bluetooth communication module.

Further, referring to FIG. 3, in the present embodiment, in addition to the battery, the power supply module 17 further includes the charging interface 171, the power indicator light 172 and the work status light 173. Specifically, the charging interface 171 is connected to an external power source to charge the battery. In a preferred solution of the present embodiment, the charging interface 171 is a Universal Serial Bus (USB) interface, and meanwhile, the charging interface 171 can also communicate with an external device. The power indicator light 172 can indicate whether the power supply module 17 is working properly by the on/off state. The work status indicator light 173 can also indicate whether the entire mobile terminal device is working properly by the on/off state.

Further, referring to FIG. 3, in the present embodiment, the mobile terminal device shown in FIG. 1 further includes the control panel 19, and a plurality of preset control buttons are arranged on the control panel 19, and each preset control button is configured to control the mobile terminal device 1 to perform the corresponding operation. For example, the preset control button can be a start-stop button capable of controlling the start or stop of the mobile terminal device 1. The preset control button can also be a data query button capable of controlling the mobile terminal device 1 to display the real-time or historical work data through the display module 14.

Further, in the present embodiment, the processing device 2 shown in FIG. 1 can perform data analysis on the blood oxygen information obtained by mobile terminal device 1 as follows: drawing and displaying the distribution map of the blood oxygen of the detected subject according to the received blood oxygen information, and/or comparing the received blood oxygen information with the preset sample, and determining the distribution mode of the current blood oxygen information according to the comparison result to facilitate the state judgment of the detected subject, such as disease status.

Those skilled in the art can understand that the aforementioned non-contact brain blood oxygen detecting device further includes other well-known structures, such as a processor, a controller, a memory, a display a user interface and so on each connected so as to be operable, as known by skilled artisans. The memory includes, but is not limited to, a random memory, a flash memory, a read-only memory, a programmable read-only memory, a volatile memory, a non-volatile memory, a serial memory, a parallel memory, a register and others. The processor includes, but is not limited to, a complex programmable logic device/field programmable gate array (CPLD/FPGA), a digital signal processor (DSP), an advanced reduced instruction set computing machine (ARM) processor, a million instructions per second (MIPS) processor, and others. In order not to obscure the present embodiment of the present invention, these well-known structures are not shown in FIGS. 1-3.

In addition, it is understood by those skilled in the art that although some of the present embodiments described herein include some characteristics rather than other characteristics in other embodiments, the characteristics of different embodiments can be combined to form new differents embodiment which shall fall within the scope of the present invention. For example, in the claims for the present invention, any one of the present embodiments claimed for protection may be used in any combination.

It should be noted that the above embodiments illustrate the present invention rather than limiting it, and that those skilled in the art may design a replacement embodiment without deviating from the scope of the appended claims. In the claim, no reference symbol between parentheses should be constructed to limit the claim. The word "include/comprise" does not exclude the presence of elements or steps not listed in the claims. The word "a" or "one" that precedes a component does not exclude the presence of multiple such components. The present invention can be implemented by means of hardware including several different elements and personal computer (PC) with proper programming. In the unit claims enumerating several devices, several of these devices may be implemented by the same hardware item. The use of words, e.g. first, second, third and the like, does not indicate any order, and these words can be interpreted as names.

Hereto, the technical solution of the present invention has been described in conjunction with the preferred embodiments shown in the drawings, but it is easy for those skilled in the art to understand that the scope of protection of the present invention is obviously not limited to these specific embodiments. Equivalent changes or replacements to the relevant technical characteristics can be made by those skilled in the art without deviating from the principles of the present invention, and the technical solutions resulting from these changes or replacements shall fall within the scope of protection of the present invention.

What is claimed is:

1. A non-contact brain blood oxygen detecting system, comprising a mobile terminal device, wherein the mobile terminal device comprises:
    a transmitter to emit dual-wavelength near-infrared light to a detected subject;
    a receiver to receive a light signal, wherein the light signal is propagated from the transmitter and fed back by the detected subject, and the receiver is further configured to perform data conversion on the light signal to obtain a digital signal containing blood oxygen information;

a first rotator attached to the mobile terminal device and arranged on the transmitter to rotate a first specific angle to change a transmitting direction of the transmitter;

a second rotator attached to the mobile terminal device and arranged on the receiver to rotate a second specific angle to change a receiving direction of the receiver;

a controller to obtain the blood oxygen information of the detected subject according to the digital signal obtained by the receiver; and a display to display the blood oxygen information obtained by the controller.

2. The non-contact brain blood oxygen detecting system according to claim 1, wherein, a light filter is arranged on the receiver to filter out an interference light signal.

3. The non-contact brain blood oxygen detecting system according to claim 2, wherein, a passband range of the light filter is 600-1000 nm.

4. The non-contact brain blood oxygen detecting system according to claim 2, wherein, the mobile terminal device further comprises a memory, a clock, a power supply and a communication interface;

the memory is configured to store working data of the mobile terminal device;

the clock is configured to provide a working clock signal to the mobile terminal device;

the power supply is configured to supply power to the mobile terminal device; and the communication is configured to communicate with an external device.

5. The non-contact brain blood oxygen detecting system according to claim 2, wherein, comprising only one transmitter and two receivers.

6. The non-contact brain blood oxygen detecting system according to claim 2, further comprising a processing device, wherein, the processing device is connected to and communicates with the mobile terminal device; and the processing device is configured to receive the blood oxygen information obtained by the controller in the mobile terminal device, and the processing device is further configured to perform data analysis on the blood oxygen information and display the blood oxygen information.

7. The non-contact brain blood oxygen detecting system according to claim 1, wherein, the mobile terminal device further comprises a memory, a clock, a power supply and a communication interface;

the memory is configured to store working data of the mobile terminal device;

the clock is configured to provide a working clock signal to the mobile terminal device;

the power supply is configured to supply power to the mobile terminal device; and the communication interface is configured to communicate with an external device.

8. The non-contact brain blood oxygen detecting system according to claim 7, wherein, the power supply comprises a battery and a charging interface, and the charging interface is configured to connect to an external power source to charge the battery; and the charging interface is a USB interface, and the USB interface is further configured to communicate with the external device.

9. The non-contact brain blood oxygen detecting system according to claim 7, wherein, the communication interface is Bluetooth.

10. The non-contact brain blood oxygen detecting system according to claim 7, wherein, the mobile terminal device further comprises a control panel, and a plurality of preset control buttons are arranged on the control panel; and the plurality of preset control buttons are configured to control the mobile terminal device to perform operations respectively corresponding to the plurality of preset control buttons.

11. The non-contact brain blood oxygen detecting system according to claim 1, comprising only one transmitter and two receivers.

12. The non-contact brain blood oxygen detecting system according to claim 11, wherein the distances between the two receivers and the transmitter are 3 cm and 4 cm, respectively.

13. The non-contact brain blood oxygen detecting system according to claim 1, further comprising a processing device, wherein, the processing device is connected to and communicates with the mobile terminal device; and the processing device is configured to receive the blood oxygen information obtained by the controller in the mobile terminal device, and the processing device is further configured to perform data analysis on the blood oxygen information and display the blood oxygen information.

14. The non-contact brain blood oxygen detecting system according to claim 1, wherein the controller further compares the obtained blood oxygen information of the detected subject to a preset sample and generates a disease status of the detected subject based on a result of the comparison; and wherein the display further displays the generated disease status of the detected subject.

* * * * *